(12) United States Patent
Hou et al.

(10) Patent No.: US 10,550,688 B2
(45) Date of Patent: Feb. 4, 2020

(54) APPARATUS FOR PHYSICAL SIMULATION EXPERIMENT FOR FRACTURING IN HORIZONTAL WELL LAYER BY LAYER BY SPIRAL PERFORATION AND METHOD THEREOF

(71) Applicant: China University of Petroleum—Beijing, Beijing (CN)

(72) Inventors: Bing Hou, Beijing (CN); Zhi Chang, Beijing (CN); Yan Jin, Beijing (CN); Mian Chen, Beijing (CN); Yunhu Lu, Beijing (CN); Botao Lin, Beijing (CN); Zhou Zhou, Beijing (CN); Peng Tan, Beijing (CN)

(73) Assignee: China University of Petroleum—Beijing, Beijing (CN)

( * ) Notice: Subject to any disclaimer, the term of this patent is extended or adjusted under 35 U.S.C. 154(b) by 221 days.

(21) Appl. No.: 15/858,283

(22) Filed: Dec. 29, 2017

(65) Prior Publication Data
US 2019/0055838 A1 Feb. 21, 2019

(30) Foreign Application Priority Data
Aug. 15, 2017 (CN) .......................... 2017 1 0695634

(51) Int. Cl.
*E21B 47/10* (2012.01)
*E21B 43/26* (2006.01)
(52) U.S. Cl.
CPC .............. *E21B 47/10* (2013.01); *E21B 43/26* (2013.01)
(58) Field of Classification Search
CPC .................................. E21B 47/10; E21B 43/26

USPC ....................................................... 73/152.39
See application file for complete search history.

(56) References Cited

U.S. PATENT DOCUMENTS

| 3,754,446 A | * | 8/1973 | O'Connor | G01F 23/62 |
| | | | | 73/453 |
| 6,415,869 B1 | * | 7/2002 | Smith | E21B 17/028 |
| | | | | 166/381 |
| 2005/0126300 A1 | * | 6/2005 | Go Boncan | G01N 3/08 |
| | | | | 73/803 |
| 2008/0210422 A1 | * | 9/2008 | Clark | E21B 33/124 |
| | | | | 166/254.2 |
| 2012/0132416 A1 | * | 5/2012 | Zolezzi-Garreton | E21B 28/00 |
| | | | | 166/249 |

* cited by examiner

*Primary Examiner* — Justin Seo
*Assistant Examiner* — Rodney T Frank
(74) *Attorney, Agent, or Firm* — Caesar Rivise, PC (57) ABSTRACT

Apparatus and method for a physical simulation experiment of fracturing an unconventional oil and gas reservoir layer by layer by spiral perforation via a horizontal well bore. The apparatus includes an outer wellbore provided with at least three layers of spiral perforations, and an inner wellbore provided with at least three layers of through-holes. The method includes injecting fracturing fluid into the inner wellbore, and opening a first layer cracks of a stratum by the fracturing fluid passing the first through-hole layer and the first spiral perforation layer, opening a second layer cracks of the stratum by the fracturing fluid passing second through-hole layer and second spiral perforation layer and opening a third layer cracks of the stratum by the fracturing fluid passing third through-hole layer and third spiral perforation layer.

20 Claims, 6 Drawing Sheets

APPARATUS FOR PHYSICAL SIMULATION EXPERIMENT FOR FRACTURING IN HORIZONTAL WELL LAYER BY LAYER BY SPIRAL PERFORATION AND METHOD THEREOF

TECHNICAL FIELD

The present invention relates generally to field of technology for oil and gas development, and more particularly relates to apparatus for physical simulation experiment for fracturing in horizontal well layer by layer by spiral perforation and method thereof.

BACKGROUND OF THE INVENTION

Unconventional oil and gas reservoirs, such as shale oil and gas, coal gas and tight oil and gas and so on, are widely distributed in China and prospective reserves thereof are huge. As such high-efficiency exploitation of unconventional oil and gas reservoirs is a long-term focus in the petroleum industry. An unconventional oil and gas reservoir exhibits the feature of low pore and low permeability. Thus, the high-efficiency exploitation of an unconventional oil reservoir needs large-scale hydraulic fracturing operations to form a large number of and even net-like cracks, with high diversion ability in the reservoir, so that migration conditions for oil and gas are improved.

Multistage hydraulic fracturing is a fracturing and completion method commonly used in horizontal wells. With this method, a large number of hydraulic cracks could be formed at different positions in one reservoir, so that oil and gas drainage volume of the unconventional oil and gas reservoir is increased and resistance for oil and gas migration is reduced. However, stress interference and communication in multistage hydraulic crack determines success rate of hydraulic fracturing in oilfield and the efficiency of the hydraulic crack, which determines directly subsequent exploitation speed of the reservoir and economic benefit. At present, domestic and foreign research institutes are actively seeking to characterize the mechanical mechanism of the interaction of the cracks, studying the stress interference among the cracks through method of indoor physical simulation, and forming a complex fracture network effectively using this interference.

SUMMARY OF THE INVENTION

In order to solve the problem in the prior arts, the invention provides an apparatus for physical simulation experiment for fracturing in horizontal well layer by layer by spiral perforation, comprising an outer wellbore and an inner wellbore, the inner wellbore is positioned in the outer wellbore; further comprising an electrical machinery, a locating shell and a displacement transducer, the electrical machinery is set in the locating shell, one end of the outer wellbore is connected with the locating shell; one end of the displacement transducer is connected with the electrical machinery, the other end of the displacement transducer is connected with one end of the inner wellbore; the outer wellbore is provided with at least three layers of spiral perforations, and the inner wellbore is provided with at least three layers of through-holes.

Preferably, the displacement transducer is composed of a connecting rod and a D-shaped hollow cavity, and a part where the connecting rod is connected with the D-shaped hollow cavity is provided with thread.

Additional three circles of outer thread on the displacement transducer are provided for standby; length of inner thread of the outer wellbore is greater than maximum moving distance of the inner wellbore; distance from bottom of hole at the bottom of the outer wellbore to the top of the inner thread of the outer wellbore is greater than sum of length of the connecting rod and distance from the last sealing ring to the bottom of the inner wellbore.

Any one of above solutions, preferably, one end of the outer wellbore is provided with a wellhead, the other end of the outer wellbore is provided with a lug boss, and external surface of the lug boss is provided with thread; inner surface of the outer wellbore is provided with thread at the end near to the lug boss.

Any one of above solutions, preferably, closed end of the inner wellbore is provided with a clamping slot, open end of the inner wellbore is communicated with the wellhead at one end of the outer wellbore; the clamping slot is cooperatively connected with one end of the connecting rod.

Any one of above solutions, preferably, the electrical machinery is provided with a motor shaft, the motor shaft is D-shaped shaft, and the motor shaft is cooperatively connected with the D-shaped hollow cavity.

Any one of above solutions, preferably, the locating shell is provided with two symmetrical limiting platforms at the bottom and thread at connecting part, and a receiving cavity is formed between the limiting platforms and the connecting part. The locating shell not only could fix the electrical machinery, and also be connected with the outer wellbore by thread, acting as sealing.

Any one of above solutions, preferably, the connecting part of the locating shell is connected with the lug boss at one end of the outer wellbore by thread.

Any one of above solutions, preferably, the electrical machinery is fixed between the two limiting platforms at the bottom of the locating shell.

Any one of above solutions, preferably, a remote control circuit board and a battery are received in the receiving cavity. The remote control circuit board could realize function of switching on, switching off and clockwise/anticlockwise rotation of the electrical machinery.

Any one of above solutions, preferably, the receiving cavity is used to receive the electrical machinery, the motor shaft and the D-shaped hollow cavity of the displacement transducer.

Any one of above solutions, preferably, length of the D-shaped hollow cavity is sum of moving distance of the inner wellbore, minimum cooperative length of the motor shaft and the D-shaped hollow cavity, minimum gap between the motor shaft and the closed end of the D-shaped hollow cavity.

The motor shaft is cooperatively connected with the D-shaped hollow cavity of the displacement transducer to drive the displacement transducer to move. The connecting rod of the displacement transducer is cooperatively connected with the clamping slot at the closed end of the inner wellbore to drive the inner wellbore to move. Length of the motor shaft is greater than the maximum moving distance of the inner wellbore, and original cooperative length of the motor shaft and the D-shaped hollow cavity is at least 2 mm, so that transmitting of torque could be ensured, and at least 1 mm gap between the top of the motor shaft and the closed end of the D-shaped hollow cavity could be ensured. Switching on, switching off and clockwise/anticlockwise rotation of the electrical machinery all could be remotely controlled by telecontrol, and rotation time of the electrical machinery could be determined by a timer.

Any one of above solutions, preferably, the outer wellbore is provided with three layers of spiral perforations, and the inner wellbore is provided with three layers of through-holes.

Any one of above solutions, preferably, the three layers of spiral perforations are sequentially arranged from the lug boss to the wellhead, and are respectively a first spiral perforation layer, a second spiral perforation layer and a third spiral perforation layer; the three layers of through-holes are sequentially arranged from the closed end of the inner wellbore to its open end, and are respectively a first through-hole layer, a second through-hole layer and a third through-hole layer.

Any one of above solutions, preferably, at least one circle of spiral perforation are simulated in perforation section of each spiral perforation layer of the outer wellbore, and at least three through-holes are provided on each circle; diameter of the spiral perforation is not less than 1 mm.

Any one of above solutions, preferably, distance L between adjacent two spiral perforation layers on the outer wellbore is not less than 20 mm. In the perforation section of each spiral perforation layer of the outer wellbore, the perforations are configured in a spiral manner from the lug boss to the wellhead. The first perforation is starting point of the perforation section, and the last perforation is terminal thereof. The distance between adjacent spiral perforation layers is the distance between two terminals of adjacent two spiral sections.

Any one of above solutions, preferably, two through-holes are provided on each through-hole layer of the inner wellbore, and the two through-holes are evenly provided on the through-hole layer; height of the through-hole is not less than 0.5 mm.

Any one of above solutions, preferably, grooves are respectively provided on two sides of through-hole of each through-hole layer, and sealing rings are provided in the grooves; an annular cavity is formed by the sealing rings, inner wellbore and outer wellbore. The through-hole is used to communicate the interior of the inner wellbore with the spiral perforation of the outer wellbore, i.e. to communicate the interior of the inner wellbore with the ground; the sealing ring could be used to simulate a packer or drill-able bridge plug on site.

Sealing mechanism of O-shaped sealing ring: O-shaped sealing ring is also called as O-shaped ring, and is a rubber ring with circle cross-section. The O-shaped to sealing ring is a sealing component widely used in hydraulic and pneumatic system. The O-shaped ring has good sealing property, could be used for static seal, and also can be used for reciprocating seal; the O-shaped ring not only can be used alone, and also is essential part of many modular seals. The O-shaped ring has very wide applying range, if its material is chosen properly, the O-shaped ring can satisfy kinds of requirements of movement condition. For example, its work pressure could range from $1.333*10^5$ Pa to 400 MPa. and its temperature could range from 60° C. below zero to 200° C. Compared with other seals, the O-shaped ring has following features: 1) small size, easy assembly and dis-assembly; 2) suitable for static and dynamic seals, almost no leakage for static seal; 3) two-way seal with single O-shaped ring; 4) less dynamic friction resistance; 5) low price. The O-shaped ring is an exclusion seal, and the work principle is as follows: relying on elastic deformation of seal component, resulting in contact pressure on the sealing contact surface, if the contact pressure is greater than inner pressure of the sealed medium, and no leakage will occur; on the contrary, leakage will occur.

Any one of above solutions, preferably, "H" refers to distance between outer surfaces of two sealing rings on each through-hole layer in the inner wellbore, H>h+2a, wherein, "h" refers to height of the perforation section, and h≥5 mm; "a" refers to thickness of the sealing ring, and a≥2 mm.

Any one of above solutions, preferably, "L'" refers to distance between adjacent two through-hole layers in the inner wellbore. L'≥_L+H, wherein, "L" refers to distance between adjacent two spiral perforation layers in the outer wellbore, and "H" refers to distance between outer surfaces of two sealing rings on each through-hole layer in the inner wellbore. The through-hole of each through-hole layer in the inner wellbore is provided with sealing rings on both sides, from the closed end to the open end of the inner wellbore, respectively called first sealing ring and second sealing ring. The distance between adjacent two through-hole layers is the distance between outer surfaces of two sealing rings on each through-hole layer.

Any one of above solutions, preferably, distance from the outer side of the first sealing ring for the first through-hole layer in the inner wellbore to the thread on inner surface of the outer wellbore is not less than 2H, and H refers to distance between outer surfaces of two sealing rings on through-hole layer.

It is necessary to take several parameters into consideration to perforate spirally different rock cracks in turn, such as the distance between adjacent spiral perforation layers in the outer wellbore, the distance between adjacent through-hole layers in the inner wellbore, the thickness of the sealing ring and the height of the perforation section etc.

The invention also provides a method for physical simulation experiment for fracturing in horizontal well layer by layer by spiral perforation, comprising following steps in sequence:

Step 1: according to requirement of experiment, providing the outer wellbore with spiral perforations, providing the inner wellbore with through-holes, and installing sealing rings on both sides of the through-holes; assembling the outer wellbore, the inner wellbore, the electrical machinery, locating shell and displacement transducer together to form an apparatus for physical simulation experiment for multi-stage hydraulic fracturing in horizontal well; checking the apparatus, and ensuring the sealing good:

Step 2: filling sponge into the spiral perforation in the outer wellbore; fixing the apparatus in a mold, pouring pre-prepared grout into the mold, after solidification of the grout, taking out concrete sample from the mold to work as rock core sample; connecting the wellhead of the outer wellbore with fracturing equipment, and then starting simulation experiment;

Step 3: confirming starting position of the inner wellbore by remote controlling, i.e. the first through-hole layer of the inner wellbore aligning with the first spiral perforation layer of the outer wellbore; injecting fracturing fluid into the inner wellbore, and opening a first layer cracks of the rock core sample by the fracturing fluid passing the first through-hole layer and the first spiral perforation layer;

Step 4: switching on the electrical machinery by remote controlling, the displacement transducer driving the inner wellbore to move toward the receiving cavity of the locating shell, after the second through-hole layer of the inner wellbore aligning with the second spiral perforation layer of the outer wellbore, continuing to injecting fracturing fluid into the inner wellbore, opening a second layer cracks of the rock core sample by the fracturing fluid passing the second through-hole layer and the second spiral perforation layer;

Step 5: switching on the electrical machinery by remote controlling, the displacement transducer continuing to drive the inner wellbore to move toward the receiving cavity of the locating shell, after the third through-hole layer of the inner wellbore aligning with the third spiral perforation layer of the outer wellbore, continuing to injecting fracturing fluid into the inner wellbore, opening a third layer cracks of the rock core sample by the fracturing fluid passing the third through-hole layer and the third spiral perforation layer.

Preferably, the apparatus is any one of mentioned apparatus for physical simulation experiment for fracturing in horizontal well layer by layer by spiral perforation.

The apparatus for physical simulation experiment for fracturing in horizontal well layer by layer by spiral perforation and method thereof provided in the invention provide double layer wellbores for hydraulic fracture on the basis of hydraulic fracture device with real three axes. Movement of the inner wellbore in the outer wellbore could be controlled by controlling remotely the electrical machinery connected with the displacement transducer to communicate the spiral perforation on the outer wellbore with the through-hole on the inner wellbore corresponding to the spiral perforation, so that different stratum could be opened spirally. The outer wellbore is consolidated inside the rock core, the displacement transducer is driven by the electrical machinery by telecontrol, and further the inner wellbore is driven to move to different place so that different stratum is fractured, in the case, the stratum could be fractured infinitely when no leakage of pressure occurs at mouth of well. Configuration of the spiral perforations could be adjusted according to requirement of experiment.

Compared with the prior arts, the apparatus and method provided in the invention has following advantages: (1) kinds of multistage fracture could be realized when no leakage of pressure at the mouth of well; (2) different stratum could be opened by spiral perforations to make fracture operation simple, and it is necessary only to control the electrical machinery remotely; (3) the multistage fracture can be finished in one wellbore; (4) real fracture can be simulated under laboratory conditions to provide more liable reference for real work.

Wherein, notes in the drawings: 1—outer wellbore, 2—inner wellbore, 3—electrical machinery, 4—locating shell, 5—displacement transducer, 6—D—shaped hollow cavity, 7—connecting rod, 8—spiral perforation, 9—through-hole, 10—wellhead, 11—lug boss, 12—clamping slot, 13—sealing ring, 14—motor shaft, 15—limiting platform, 14—connecting part, 17—receiving cavity, 18—rock core sample.

DETAILED DESCRIPTION OF PREFERRED EMBODIMENTS

In order to further understand the invention, detailed examples would be described in detail.

Embodiment 1

In FIGS. 1-13, there is shown apparatus for physical simulation experiment for fracturing in horizontal well layer by layer by spiral perforation. The apparatus comprises an outer wellbore 1 and an inner wellbore 2. The inner wellbore 2 is configured in the outer wellbore 1. The apparatus also comprises an electrical machinery 3, a locating shell 4 and a displacement transducer 5. The electrical machinery 3 is configured in the locating shell 4. One end of the outer wellbore 1 is connected with the locating shell 4. One end of the displacement transducer 5 is connected with the electrical machinery 3. The other end of the displacement transducer 5 is connected with one end of the inner wellbore 2. The outer wellbore 1 is provided with three layers of spiral perforations 8. The inner wellbore 2 is provided with three layers of through-holes 9.

Figure 12:
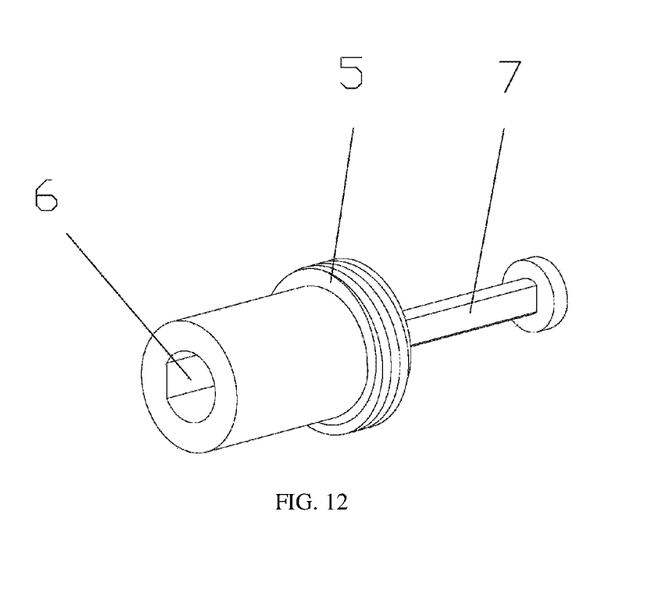
FIG. 12 is structure schematic diagram of a preferred displacement transducer of the apparatus shown in FIG. 1.

As best seen in FIG. 12, the displacement transducer 5 is composed of a connecting rod 7, and a D-shaped hollow cavity 6, with a portion of the displacement transducer where the connecting rod 7 is connected to the D-shaped hollow cavity 6 being in the form of a thread. The outer wellbore 1 is provided with a wellhead 10 at one end and a lug boss 11 at the other end thereof. The lug boss 11 is configured with thread on outer surface thereof. The outer wellbore 1 is configured with thread on its inner surface at the end near by the lug boss 11. The closed end of the inner wellbore 2 is provided with a clamping slot 12. The open end of the inner wellbore 2 is in communication with the wellhead 10 at one end of the outer wellbore 1. The clamping slot 12 is cooperatively connected with one end of the connecting rod 7. The electrical machinery 3 is provided with a motor shaft 14. The motor shaft 14 is a D-shaped shaft. The motor shaft 14 is cooperatively connected with the D-shaped hollow cavity 6.

Figure 10:
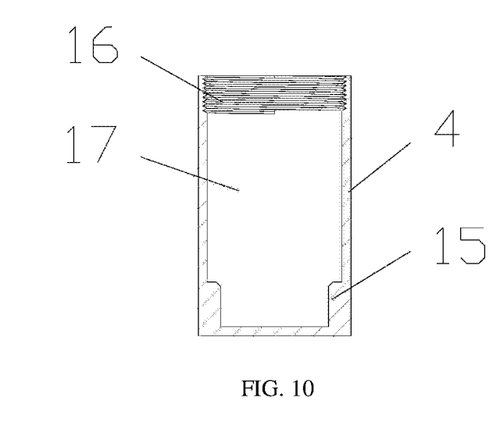
FIG. 10 is section view of a preferred locating shell of the apparatus shown in FIG. 1.
Figure 11:
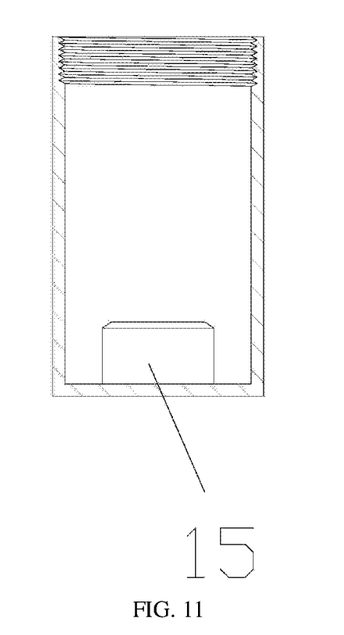
FIG. 11 is another section view of a preferred locating shell of the apparatus shown in FIG. 1.

As best seen in FIGS. 10 and 11 the locating shell 4 is provided with two symmetrical limiting platforms 15 at the bottom thereof. The connecting part of the locating shell 4 is provided with a thread 16, and a receiving cavity 17 is formed between the limiting platforms 15 and the connecting part 16. The connecting part 16 of the locating shell 4 is connected with the lug boss 11 at one end of the outer wellbore 1 by a thread. The electrical machinery 3 is fixed between the two limiting platforms 15 at the bottom of the locating shell 4. A remote control circuit and a battery are received in the receiving cavity 17. The receiving cavity 17 is used to receive the electrical machinery 3, the motor shaft 14 and the D-shaped hollow cavity 6 of the displacement transducer 5. The length of the D-shaped hollow cavity is sum of the moving distance of the inner wellbore, the minimum cooperative length of the motor shaft and the D-shaped hollow cavity, the minimum gap between the motor shaft and the closed end of the D-shaped hollow cavity.

The motor shaft is cooperatively connected with the D-shaped hollow cavity of the displacement transducer, which will drive the displacement transducer to move. The connecting rod of the displacement transducer is cooperatively connected with the clamping slot at the closed end of the inner wellbore, and further movement of the inner wellbore is driven. The length of the motor shaft is greater than maximum moving distance of the inner wellbore. The original cooperative length of the motor shaft with the D-shaped hollow cavity is at least 2 mm, so that transmitting of torque could be ensured, and at least 1 mm gap between the top of the motor shaft and the closed end of the D-shaped hollow cavity could be ensured. The electrical machinery could be switched on and off remotely by telecontrol. Also, clockwise/clockwise rotation of the electrical machinery could be remotely controlled by telecontrol, and rotation time could be determined by a timer.

The three layers of spiral perforations are sequentially configured from the lug boss to the wellhead, and are respectively a first spiral perforation layer, a second spiral perforation layer and a third spiral perforation layer. The three layers of through-holes are sequentially configured from the closed end of the inner wellbore to its open end, and are respectively a first through-hole layer, a second through-hole layer and a third through-hole layer.

One circle of spiral perforation is simulated in perforation section of each spiral perforation layer of the outer wellbore, and three through-holes are provided on each circle. The diameter of the spiral perforation is 1 mm.

The distance "L" between adjacent two spiral perforation layers on the outer wellbore is 20 mm. In the perforation section of each spiral perforation layer of the outer wellbore, the perforations are configured in a spiral manner from the lug boss to the wellhead. The first perforation is the starting point of the perforation section, and the last perforation is the terminal thereof. The distance between adjacent spiral perforation layers is the distance between two terminals of adjacent two spiral sections.

Two through-holes are provided on each through-hole layer of the inner wellbore, and the two through-holes are evenly provided on the through-hole layer. The height of the through-hole is 0.5 mm.

Figure 1:
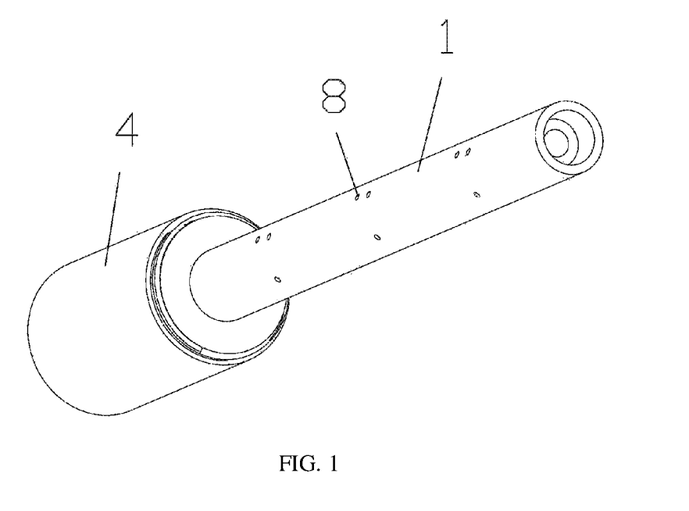
FIG. 1 is total structure schematic diagram of a preferred example of apparatus for physical simulation experiment for fracturing in horizontal well layer by layer by spiral perforation provided in the invention.
Figure 2:
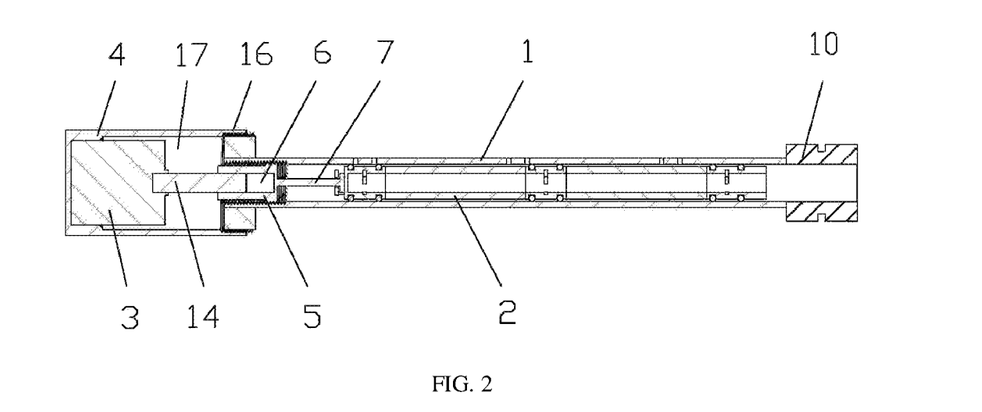
FIG. 2 is section view of the apparatus shown in FIG. 1.
Figure 3:
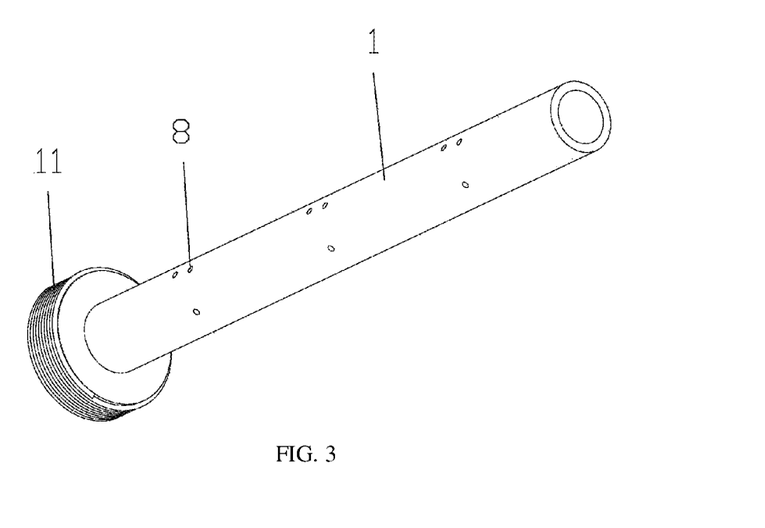
FIG. 3 is structure schematic diagram of a preferred outer wellbore of the apparatus shown in FIG. 1.
Figure 4:
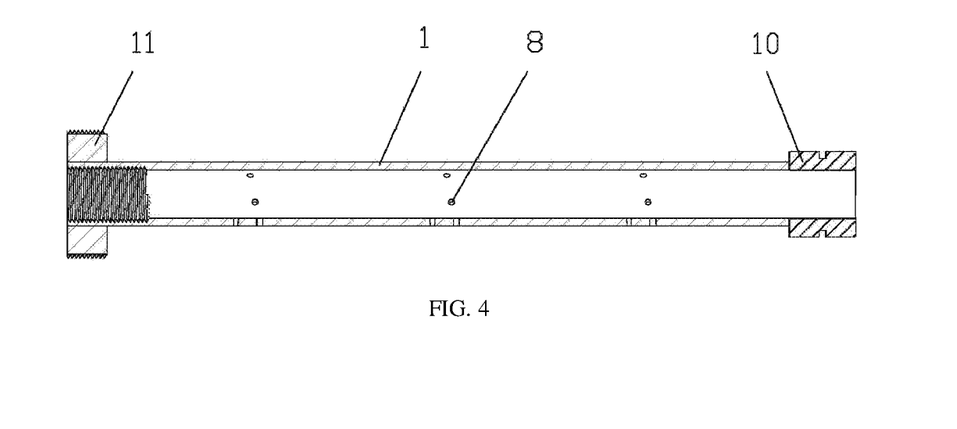
FIG. 4 is section view of the outer wellbore of the apparatus shown in FIG. 1.
Figure 5:
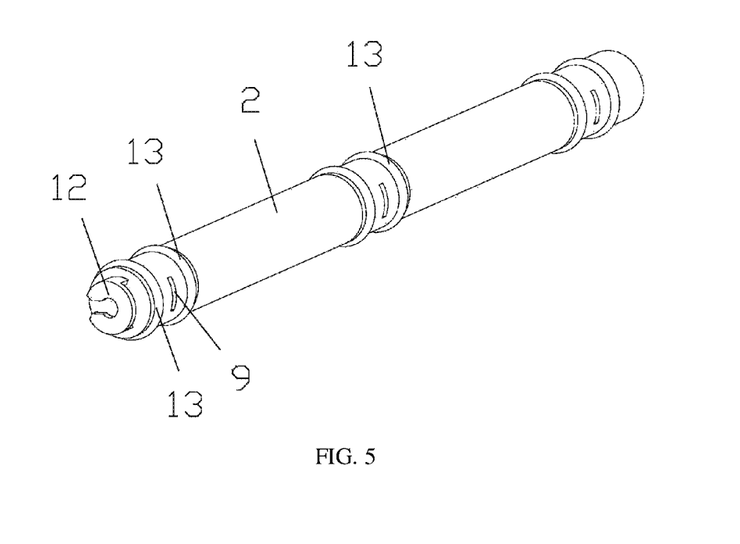
FIG. 5 is structure schematic diagram of a preferred inner wellbore of the apparatus shown in FIG. 1.
Figure 6:
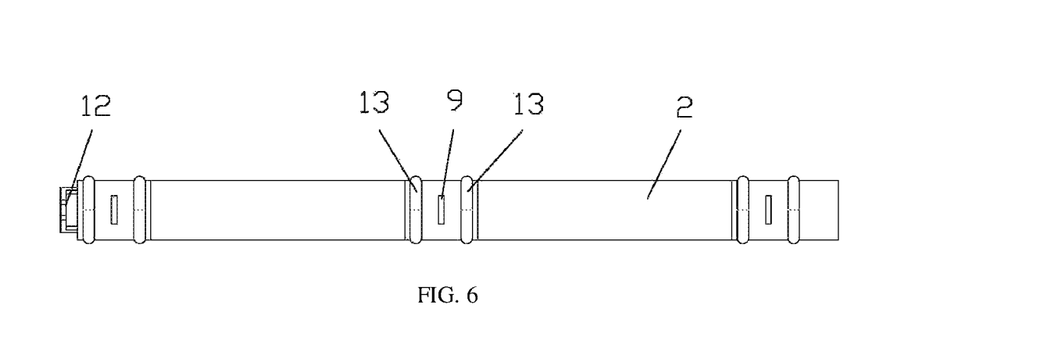
FIG. 6 is another section view of inner wellbore of the apparatus shown in FIG. 1.
Figure 7:
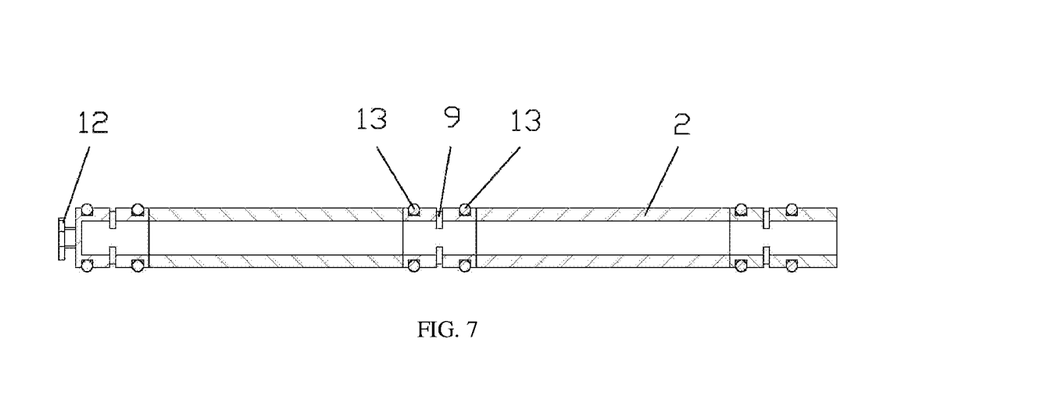
FIG. 7 is section view of the inner wellbore of the apparatus shown in FIG. 1.
Figure 8:
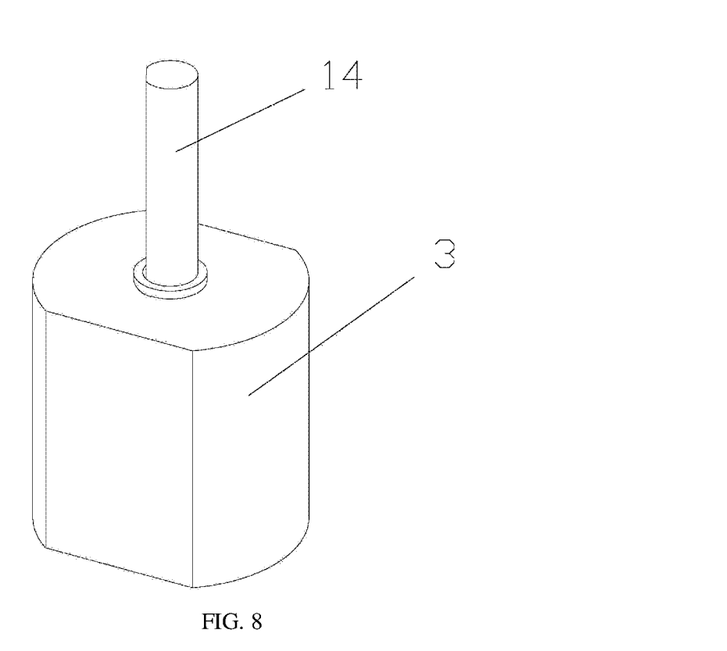
FIG. 8 is structure schematic diagram of a preferred electrical machinery of the apparatus shown in FIG. 1.
Figure 9:
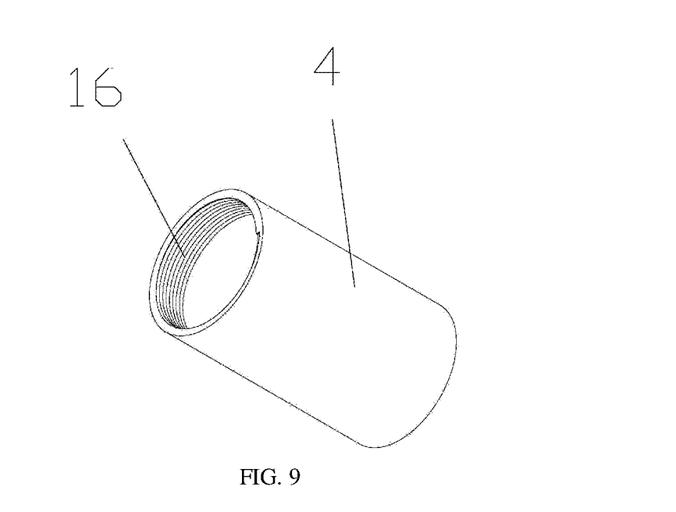
FIG. 9 is structure schematic diagram of a preferred locating shell of the apparatus shown in FIG. 1.

As best seen in FIGS. 5-7 grooves are respectively provided on two sides of through-hole 9 of each through-hole layer. Sealing rings 13 are provided in the grooves. An annular cavity is formed by the sealing rings 13, the inner wellbore 2 and the outer wellbore 1. The through-hole is used to communicate the interior of the inner wellbore with the spiral perforation of the outer wellbore, i.e. to communicate the interior of the inner wellbore with the ground. The sealing ring could be used to simulate a packer or drill-able bridge plug on site.

"H" refers to distance between outer surfaces of two sealing rings on each through-hole layer in the inner wellbore, and $H > h + 2a$, wherein, "h" refers to the height of the perforation section, and h=5 mm; "a" refers to thickness of the sealing ring, and a=2 mm.

"L'" refers to distance between adjacent two through-hole layers in the inner wellbore, and $L' \geq L + H$. "L" refers to distance between adjacent two spiral perforation layers in the outer wellbore. "H" refers to distance between outer surfaces of two sealing rings on each through-hole layer in the inner wellbore. The through-hole of each through-hole layer in the inner wellbore is provided with sealing rings on both sides, from the closed end to the open end of the inner wellbore, respectively called a first sealing ring and a second sealing ring. The distance between adjacent two through-hole layers is the distance between outer surfaces of two sealing rings on each through-hole layer.

The distance from the outer side of the first sealing ring for the first through-hole layer in the inner wellbore to the thread on inner surface of the outer wellbore is not less than 2H, and "H" refers to distance between outer surfaces of two sealing rings on through-hole layer.

In the embodiment shown, it is necessary to take several parameters into consideration to perforate spirally different rock cracks in turn, such as the distance between adjacent spiral perforation layers in the outer wellbore, the distance between adjacent through-hole layers in the inner wellbore, the thickness of the sealing ring and the height of the perforation section.

Figure 13:
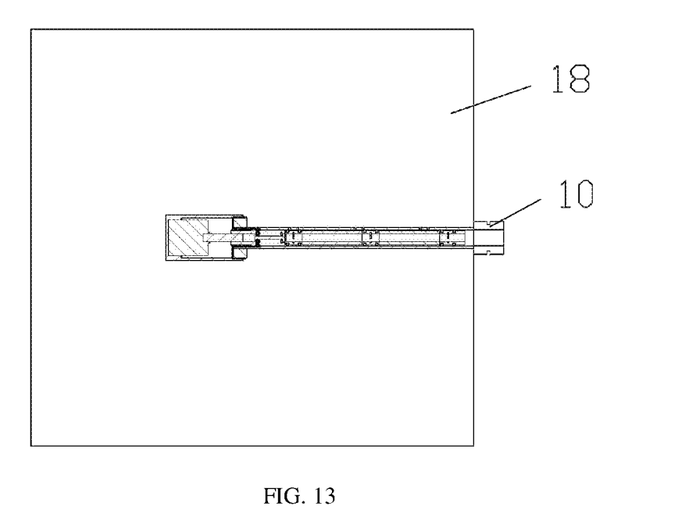
FIG. 13 is schematic diagram of rock core sample for the apparatus shown in FIG. 1.

A method for physical simulation experiment for fracturing in horizontal well layer by layer by spiral perforation is also provided in accordance with this invention. The method comprises the following steps in sequence:

Step 1: according to requirement of the experiment, providing the outer wellbore 1 with spiral perforations 8, providing the inner wellbore 2 with a through-hole 9, and installing sealing rings 13 on both sides of the through-hole 9; assembling the outer wellbore 1, the inner wellbore 2, and the electrical machinery 3, locating shell 4 and displacement transducer 5 together to form an apparatus for physical simulation experiment for multistage hydraulic fracturing in a horizontal well; checking the apparatus, and ensuring that the sealing is good;

Step 2: filling sponge into the spiral perforation 8 in the outer wellbore 1; fixing the apparatus in a mold, pouring pre-prepared grout into the mold, after solidification of the grout, taking out concrete sample from the mold to work as a rock core sample 18; connecting the wellhead at one end of the outer wellbore with fracturing equipment, and then starting the simulation experiment;

Step 3: confirming the starting position of the inner wellbore 2 by remote control, i.e., the first through-hole layer of the inner wellbore aligning with the first spiral perforation layer of the outer wellbore; injecting fracturing fluid into the inner wellbore, and opening a first layer cracks of the rock core sample by the fracturing fluid passing the first through-hole layer and the first spiral perforation layer;

Step 4: switching on the electrical machinery by remote control, the displacement transducer 5 driving the inner borehole 2 to move toward the receiving cavity 17 of the locating shell 4, after the second through-hole layer of the inner wellbore aligns with the second spiral perforation layer of the outer wellbore, continuing to inject fracturing fluid into the inner wellbore, opening a second layer cracks of the rock core sample 18 by the fracturing fluid passing the second through-hole layer and the second spiral perforation layer;

Step 5: switching on the electrical machinery by remote control, the displacement transducer 5 continuing to drive the inner borehole 2 to move toward the receiving cavity 17 of the locating shell 4, after the third through-hole layer of the inner wellbore aligns with the third spiral perforation layer of the outer wellbore, continuing to inject fracturing fluid into the inner wellbore, opening a third layer cracks of the rock core sample by the fracturing fluid passing the third through-hole layer and the third spiral perforation layer.

The apparatus for physical simulation experiment for fracturing in horizontal well layer by layer by spiral perforation and method thereof provided by this invention provide double layer wellbores for hydraulic fracture on the basis of hydraulic fracture device with real three axes. Movement of the inner wellbore in the outer wellbore could be controlled by controlling remotely the electrical machinery connected with the displacement transducer to communicate the spiral perforation on the outer wellbore with the through-hole on the inner wellbore corresponding to the spiral perforation, so that different stratum could be opened spirally. The outer wellbore is consolidated inside the rock core, the displacement transducer is driven by the electrical machinery by telecontrol, and further the inner wellbore is driven to move to a different place so that a different stratum is fractured, in the case, the stratum could be fractured infinitely when no leakage of pressure occurs at mouth of the well. The configuration of the spiral perforations could be adjusted according to requirement of experiment.

Compared with the prior arts, the apparatus and method provided by this invention has following advantages: (1) kinds of multistage fracture could be realized when no leakage of pressure at the mouth of well; (2) different stratum could be opened by spiral perforations to make fracture operation simple, and it is necessary only to control the electrical machinery remotely; (3) the multistage fracture can be finished in one wellbore; and (4) real fracture can be simulated under laboratory conditions to provide more reliable reference for real work.

Embodiment 2

Another embodiment of the apparatus and method of this invention is constructed and operates the same as the embodiment 1, the only difference being the design of parameters, and particularly is as follows:

Two circles of spiral perforations are simulated in the perforation section of each spiral perforation layer of the outer wellbore, and three through-holes are provided on each circle. The diameter of the spiral perforation is 1 mm. The distance "L" between adjacent two spiral perforation layers on the outer wellbore is 40 mm. Two through-holes are provided on each through-hole layer of the inner wellbore, and the two through-holes are evenly provided on the through-hole layer. The height of the through-hole is 1.0 mm.

"H" refers to distance between outer surfaces of two sealing rings on each through-hole layer in the inner wellbore, and H>h+2a, wherein, "h" refers to height of the perforation section, and h=6 mm; "a" refers to thickness of the sealing ring, and a=3 mm.

"L'" refers to distance between adjacent two through-hole layers in the inner wellbore, and L'≥L+H, wherein, "L" refers to distance between adjacent two spiral perforation layers in the outer wellbore, and "H" refers to distance between outer surfaces of two sealing rings on each through-hole layer in the inner wellbore.

Embodiment 3

Another embodiment of the apparatus and method of this invention is constructed and operates the same as the embodiment 1, the only difference being the design of parameters, and particularly is as follows:

Three circles of spiral perforations are simulated in the perforation section of each spiral perforation layer of the outer wellbore, and three through-holes are provided on each circle. The diameter of the spiral perforation is 1 mm. The distance "L" between adjacent two spiral perforation layers on the outer wellbore is 50 mm. Two through-holes are provided on each through-hole layer of the inner wellbore, and the two through-holes are evenly provided on the through-hole layer. The height of the through-hole is 1.0 mm.

"H" refers to distance between outer surfaces of two sealing rings on each through-hole layer in the inner wellbore, and H>h+2a, wherein, "h" refers to height of the perforation section, and h=8 mm; "a" refers to thickness of the sealing ring, and a=2 mm.

"L'" refers to distance between adjacent two through-hole layers in the inner wellbore, and L'≥L+H, wherein, "L" refers to distance between adjacent two spiral perforation layers in the outer wellbore, and "H" refers to distance between outer surfaces of two sealing rings on each through-hole layer in the inner wellbore.

It should be understood by those skilled in the art that the apparatus for physical simulation experiment for fracturing in horizontal well layer by layer by spiral perforation and method thereof provided by this invention include arbitrary combination of the above summary, detailed description of the embodiments and various parts shown in the accompanying drawings. Limited by the space and to make the description concise, the combinations are not described one by one. Any modification, equivalent replacement improvement and the like made within the spirit and principle of the present invention should be included in the protection scope of the present invention.

We claim:

1. An apparatus for providing a physical simulation experiment of fracturing an unconventional oil and gas reservoir layer by layer by spiral perforation via a horizontal well, said apparatus comprising:
    an outer wellbore provided with at least three layers of spiral perforations;
    an inner wellbore positioned in the outer wellbore, the inner wellbore being provided with at least three layers of through-holes;
    a locating shell;
    a displacement transducer; and
    electrical machinery, the electrical machinery being set in the locating shell, wherein one end of the outer wellbore is connected with the locating shell, one end of the displacement transducer is connected to the electrical machinery, the other end of the displacement transducer is connected to one end of the inner wellbore.

2. The apparatus according to claim 1, wherein the displacement transducer comprises a connecting rod, a D-shaped hollow cavity, and thread connecting the connecting rod to the D-shaped hollow cavity.

3. The apparatus according to claim 2, wherein one end of the outer wellbore is provided with a wellhead, the other end of the outer wellbore is provided with a lug boss having a near end, the lug boss having an external surface provided with a thread, and wherein the outer wellbore has an inner surface provided with a thread at the end near to the lug boss.

4. The apparatus according to claim 3, wherein the inner wellbore includes a closed end provided with a clamping slot, wherein the inner wellbore has an open end in communication with a wellhead of the outer wellbore, and wherein the clamping slot is cooperatively connected with one end of the connecting rod.

5. The apparatus according to claim 4, wherein the electrical machinery is provided with a motor shaft, the motor shaft being a D-shaped shaft, and wherein the motor shaft is cooperatively connected with the D-shaped hollow cavity.

6. The apparatus according to claim 5, wherein the locating shell includes a bottom which is provided with two symmetrical limiting platforms, wherein the locating shell includes a thread at a connecting part, and a receiving cavity located between the limiting platforms and the connecting part.

7. The according to claim 6, wherein the connecting part of the locating shell is connected with the lug boss at one end of the outer wellbore by a thread.

8. The apparatus according to claim 7, wherein the electrical machinery is fixed between the two limiting platforms at the bottom of the locating shell.

9. The apparatus according to claim 8, wherein a remote control circuit board and a battery are received in the receiving cavity.

10. The apparatus according to claim 9, wherein the electrical machinery, the motor shaft and the D-shaped hollow cavity of the displacement transducer are received within the receiving cavity.

11. The apparatus according to claim 10, wherein the D-shaped hollow cavity has a length that is the sum of moving distance of the inner wellbore, minimum cooperative length of the motor shaft and the D-shaped hollow cavity and minimum gap between the motor shaft and the closed end of the D-shaped hollow cavity.

12. The apparatus according to claim 11, wherein the outer wellbore is provided with three layers of spiral perforations, and the inner wellbore is provided with three layers of through-holes.

13. The apparatus according to claim 12, wherein the three layers of spiral perforations are sequentially arranged from the lug boss to the wellhead, and are respectively a first spiral perforation layer, a second spiral perforation layer and a third spiral perforation layer, and wherein the three layers of through-holes are sequentially arranged from the closed end of the inner wellbore to its open end, and are respectively a first through-hole layer, a second through-hole layer and a third through-hole layer.

14. The apparatus according to claim 13, wherein at least one circle of spiral perforations are simulated in a perforation section of each spiral perforation layer of the outer wellbore, wherein at least three through-holes are provided on each circle, and wherein the diameter of the spiral perforation is not less than 1 mm.

15. The apparatus according to claim 14, wherein distance "L" between adjacent two spiral perforation layers on the outer wellbore is not less than 20 mm.

16. The apparatus according to claim 15, wherein two through-holes are provided on each through-hole layer of the inner wellbore, and the two through-holes are evenly provided on the through-hole layer and wherein the height of the through-hole is not less than 0.5 mm.

17. The apparatus according to claim 16, wherein grooves are respectively provided on opposite sides of the through-hole of each through-hole layer, and wherein sealing rings are provided in the grooves, and wherein an annular cavity is formed by the sealing rings, the inner wellbore and the outer wellbore.

18. The apparatus according to claim 17, wherein "H" refers to distance between outer surfaces of two sealing rings on each through-hole layer in the inner wellbore, wherein H>h+2a, wherein, "h" refers to height of the perforation section, wherein h≥5 mm, wherein "a" refers to thickness of the sealing ring, and wherein a≥2 mm.

19. The apparatus according to claim 18, wherein "L'" refers to distance between adjacent two through-hole layers in the inner wellbore, wherein L'≥L+H, wherein "L" refers to the distance between adjacent two spiral perforation layers in the outer wellbore, and wherein "H" refers to the distance between outer surfaces of two sealing rings on each through-hole layer in the inner wellbore.

20. A method for providing a physical simulation experiment of hydraulic fracturing of an unconventional oil and gas reservoir layer by layer by spiral perforation via a horizontal well, comprising:
  Step 1: providing an apparatus as set forth in claim 1, installing sealing rings on opposite sides of the through-holes; assembling the outer wellbore, the inner wellbore, and electrical machinery, locating a shell and displacement transducer together to form the apparatus; checking the apparatus, and ensuring good seals in the apparatus;
  Step 2: filling sponge into a spiral perforation in the outer wellbore; fixing the apparatus in a mold, pouring pre-prepared grout into the mold, after solidification of the grout, taking out a concrete sample from the mold to work as rock core sample; connecting the wellhead of the outer wellbore with a fracturing equipment, and then starting the simulation experiment;
  Step 3: confirming starting position of the inner wellbore by remote control via the first through-hole layer of the inner wellbore aligning with the first spiral perforation layer of the outer wellbore; injecting fracturing fluid into the inner wellbore, and opening a first layer cracks of the rock core sample by the fracturing fluid passing the first through-hole layer and the first spiral perforation layer;
  Step 4: switching on the electrical machinery by remote control, utilizing the displacement transducer to drive the inner wellbore toward the receiving cavity of the locating shell, after a second through-hole layer of the inner wellbore aligns with a second spiral perforation layer of the outer wellbore, continuing to inject fracturing fluid into the inner wellbore, opening a second layer cracks of the rock core sample by the fracturing fluid passing the second through-hole layer and the second spiral perforation layer; and
  Step 5: switching on the electrical machinery by remote control, utilizing the displacement transducer to continue to drive the inner wellbore to move toward the receiving cavity of the locating shell, after a third through-hole layer of the inner wellbore aligns with the third spiral perforation layer of the outer wellbore, continuing to injecting fracturing fluid into the inner wellbore, opening a third layer cracks of the rock core sample by the fracturing fluid passing the third through-hole layer and the third spiral perforation layer;
  wherein the apparatus is the apparatus for physical simulation experiment for fracturing in horizontal well layer by layer by spiral perforation according to claim 1.

* * * * *